United States Patent
Wolff

(10) Patent No.: US 10,953,153 B2
(45) Date of Patent: Mar. 23, 2021

(54) INFUSION DEVICE AND METHOD ALLOWING FOR DETECTING A DRIFT IN A SENSOR SIGNAL

(71) Applicant: Fresenius Vial SAS, Brézins (FR)

(72) Inventor: Rémy Wolff, Morette (FR)

(73) Assignee: Fresenius Vial SAS, Brézins (FR)

( * ) Notice: Subject to any disclaimer, the term of this patent is extended or adjusted under 35 U.S.C. 154(b) by 79 days.

(21) Appl. No.: 16/301,829

(22) PCT Filed: Apr. 21, 2017

(86) PCT No.: PCT/EP2017/059497
§ 371 (c)(1),
(2) Date: Nov. 15, 2018

(87) PCT Pub. No.: WO2017/207165
PCT Pub. Date: Dec. 7, 2017

(65) Prior Publication Data
US 2019/0143035 A1 May 16, 2019

(30) Foreign Application Priority Data
Jun. 1, 2016 (EP) .................................. 16305635

(51) Int. Cl.
*A61M 5/168* (2006.01)
*A61M 5/145* (2006.01)

(52) U.S. Cl.
CPC ...... *A61M 5/16831* (2013.01); *A61M 5/1458* (2013.01); *A61M 2005/16863* (2013.01); *A61M 2205/332* (2013.01); *A61M 2205/50* (2013.01)

(58) Field of Classification Search
CPC .............. A61M 5/1452; A61M 5/1458; A61M 5/16831; A61M 5/16854;
(Continued)

(56) References Cited

U.S. PATENT DOCUMENTS

2003/0229311 A1* 12/2003 G. Morris ........... A61M 5/1456
604/151
2014/0163522 A1* 6/2014 Alderete, Jr. ..... A61M 5/16831
604/506
(Continued)

FOREIGN PATENT DOCUMENTS

CN 103041621 4/2013
CN 104363938 2/2015
(Continued)

OTHER PUBLICATIONS

International Search Report and Written Opinion, counterpart International Appl. No. PCT/EP2017/059497 dated Aug. 8, 2017 (17 pages).
(Continued)

*Primary Examiner* — Manuel A Mendez
*Assistant Examiner* — Justin L Zamory
(74) *Attorney, Agent, or Firm* — Cook Alex Ltd.

(57) ABSTRACT

An infusion device (1) for administering a medical fluid to a patient (P) comprises a pumping mechanism (11) for exerting a force onto a delivery set (2, 3) for delivering a medical fluid from the delivery set towards a patient (P), a sensor device (14) for measuring the force exerted on the delivery set (2, 3) by the pumping mechanism (11), the sensor device (14) being constituted to output a sensor signal indicative of the force exerted onto the delivery set (2, 3), and a processor device (15) for controlling operation of the infusion device (1). Herein, the processor device (15) is constituted to perform a diagnosis routine during which a sensor signal of the sensor device (14) is obtained and compared to an expected sensor signal, to allow for detecting a drift in the sensor signal of the sensor device (14).

10 Claims, 2 Drawing Sheets

(58) Field of Classification Search
CPC .. A61M 2005/16863; A61M 2205/332; A61M 2205/50
See application file for complete search history.

(56) References Cited

U.S. PATENT DOCUMENTS

2015/0190573 A1  7/2015  Moberg et al.
2015/0374902 A1  12/2015  Chambers et al.

FOREIGN PATENT DOCUMENTS

| CN | 105188796 | 12/2015 |
| EP | 1 267 960 B1 | 5/2006 |
| WO | WO2014/100658 | 6/2014 |

OTHER PUBLICATIONS

Office Action and Search Report, corresponding Chinese application No. 201780033505, with English-language translation (dated Nov. 4, 2020) (17 pages).

* cited by examiner

INFUSION DEVICE AND METHOD ALLOWING FOR DETECTING A DRIFT IN A SENSOR SIGNAL

The present application is a U.S. National Stage of PCT International Patent Application No. PCT/EP2017/059497, filed Apr. 21, 2017, which claims priority to EP Application No. 16305635, filed Jun. 1, 2016, both of which are hereby incorporated herein by reference.

DESCRIPTION

The invention relates to an infusion device for administering a medical fluid to a patient according to the preamble of claim 1 and to a method for operating an infusion device.

An infusion device of this kind comprises a pumping mechanism for exerting a force onto a delivery set for delivering a medical fluid from the delivery set towards a patient, and a sensor device for measuring the force exerted on the delivery set by the pumping mechanism, the sensor device being constituted to output a sensor signal indicative of the force exerted onto the delivery set. A processor device serves for controlling the operation of the infusion device.

An infusion device of this kind may for example be a volumetric (peristaltic) infusion pump or a syringe infusion pump.

In a volumetric infusion pump a delivery set in the shape of an infusion line set is placed in a receptacle of the infusion device such that a pumping mechanism of the infusion device acts onto a pumping module of the infusion line set for peristaltically pumping a medical fluid through the infusion line set towards a patient. A sensor device in the shape of a force sensor herein is placed on the infusion device and is in abutment with the delivery set received on the infusion device such that via the force sensor the pressure within the infusion line set can be measured.

A syringe infusion pump, in contrast, comprises a receptacle in which a syringe having a cylindrical tube containing a medical fluid to be administered to a patient and a piston for pushing the medical fluid out of the cylindrical tube can be received. The syringe infusion pump comprises a pusher device constituting a pumping mechanism for acting onto the piston of the syringe for pushing the piston into the cylindrical tube in order to deliver the medical fluid from the cylindrical tube towards the patient. A sensor device in the shape of a force sensor herein is placed on the pusher device for measuring the force exerted onto the piston and to derive, from the force measurement, the pressure within the cylindrical tube and an infusion line connected to the cylindrical tube.

The force measurement serves, in general, to monitor an infusion operation and, in particular, to detect an occlusion in an infusion line. If an occlusion in the infusion line connected to the patient is present, the pressure in the infusion line will rise, which can be observed by the force measurements of the sensor device. If the pressure rises beyond a predefined threshold, it is concluded that an occlusion is present, such that appropriate countermeasures can be taken for releasing the occlusion or for interrupting the infusion operation.

During an infusion operation, an occlusion must reliably be detected. In turn, false alarms are to the avoided to prevent an alarm fatigue of a user. Hence, reliable force measurements allowing for an accurate estimation of the pressure within the infusion line are required.

Typically, a load cell comprising for example strain gauges is used as sensor device. A load cell of this kind may for example comprise a sensor support for example made from aluminum and a strain gauge arrangement, such as a Wheatstone bridge circuit, fixed on the sensor support. If a force is exerted on the load cell, a (bending) deformation of the sensor support will cause an electric signal within the strain gauge arrangement placed on the sensor support, such electric signal being proportional to the force exerted on the load cell and hence allowing for a force measurement.

In a load cell, a drift may occur, for example caused by a temperature variation or by an aging of the load cell, the drift possibly influencing the sensor signal provided by the load cell and thus potentially having an impact on the accuracy of the force measurement.

Herein, two different drift effects may be present. Within the so-called zero drift the output sensor signal when no force is applied to the sensor device varies, for example over time and/or over temperature. Within the so-called span drift, in contrast, the output sensor signal when a force is applied to the sensor device may change over time and/or over temperature. Both effects may have an impact on the accuracy of the force measurement.

It is an object of the instant invention to provide an infusion device and a method for operating an infusion device which allow for a reliable operation, in particular a reliable detection of an occlusion from force measurements using a sensor device.

The object is achieved by means of an infusion device comprising the features of claim 1.

Accordingly, the processor device is constituted to perform a diagnosis routine during which a sensor signal of the sensor device is obtained and compared to an expected sensor signal, to allow for detecting a drift in the sensor signal of the sensor device.

The processor device, hence, is configured and programmed to perform a diagnosis routine to detect a potential drift in the sensor signal. For this, a sensor signal is obtained and is compared to an expected sensor signal. If it is found that the obtained sensor signal, by a substantial margin, deviates from the expected sensor signal, it can be concluded that a drift has occurred such that suitable countermeasures can be taken.

For example, it can be monitored whether the sensor signal falls outside a range around the expected sensor signal. If this is the case, it may be concluded that a drift in the sensor signal has occurred, for example caused by temperature or by an aging or by another malfunction of the sensor device, for example a load cell comprising strain gauges.

The diagnosis routine may be carried out while the pumping mechanism is in operative connection with the delivery set for exerting a force onto the delivery set, or while the pumping mechanism is not in operative connection with the delivery set. In the first case, the pumping mechanism is in operative connection with the delivery set and hence in principle is enabled to act onto the delivery set for performing an infusion operation. The sensor device in this case is loaded and subjected to a force. With such a diagnosis routine, a detection of a span drift is possible. In the second case the pumping mechanism is not in operative connection with the delivery set, such that the sensor device is not loaded and hence is not subjected to a force. In this case the output signal of the sensor device should be 0 (or at least close to 0). If this is not the case, it may be concluded that a zero drift is present.

Generally, the diagnosis routine beneficially is carried out while no infusion operation is performed, hence in an idle state of the infusion device, for example prior to an infusion operation or when an infusion operation is paused.

The infusion device, in principle, can be constituted as a syringe infusion pump or as a volumetric (peristaltic) infusion pump. A diagnosis routine of the kind described herein for detecting a span drift and/or for detecting a zero drift may in general be performed both for a syringe infusion pump and a volumetric (peristaltic) infusion pump. With the diagnosis routine, it can be detected that a drift is present, and if a drift is present, suitable countermeasures can be initiated, for example for alarming a user or service personnel or for correcting the drift.

In one aspect, the processor device may be programmed to perform a first diagnosis routine for correcting a zero drift. This diagnosis routine is beneficially carried out while the pumping mechanism is not in operative connection with the delivery set and hence is not subjected to a force. In this case, the sensor signal should be (approximately) at a zero reference. If this is not the case, it can be concluded that a zero drift is present.

Generally, the sensor device comprises a zero reference corresponding to the expected sensor signal when the pumping mechanism is not in operative connection with the delivery set and hence is not subjected to a force. The zero reference hence indicates the sensor signal present in the non-loaded state of the sensor device (typically 0 or at least close to 0). If the comparison during the first diagnosis routine (in which the obtained sensor signal is compared with the expected sensor signal, namely the stored zero reference) yields that the difference of the obtained sensor signal and the expected sensor signal is larger than a first predefined threshold, the zero reference of the sensor device may be corrected using the obtained sensor signal, assuming that the obtained sensor signal is indicative of the actual zero reference which should be used for future measurements.

Within the first diagnosis routine, it for example may be checked whether the difference of the obtained sensor signal and the expected sensor signal, namely the stored zero reference, falls outside of a predefined margin (defined by a lower bound and upper bound). If this is the case, it is concluded that a zero drift is present such that the zero drift may be corrected by the actually obtained sensor signal.

For the correction, the stored zero reference may be simply replaced by the actually obtained sensor signal during the first diagnosis routine. It however is also possible to more gradually update the zero reference, for example by applying an infinite impulse response (IIR) filter or the like.

The first diagnosis routine, as said, is carried out when the pumping mechanism is not in operative connection with the delivery set. For example, for a syringe pump the first diagnosis routine may be carried out when the pusher device of the pumping mechanism is not in operative connection with the piston of a syringe. This may be detected by the infusion device for example by checking the position of a lever which needs to be activated to connect the pusher device to the piston (the lever for example activating a so-called anti-siphon arm which grabs a piston head of the piston and holds the piston head in place with respect to the pusher device).

A second diagnosis routine may be carried out in order to detect a span drift of the sensor device. For example, in case of a syringe pump comprising a pusher device, which by means of the anti-siphon arm is configured to fix the piston with respect to the pusher device and hence to operatively connect the piston to the pusher device, the second diagnosis routine may be carried out while the anti-siphon arm fixes the piston with respect to the pusher device and hence operatively connects the piston of the syringe to the pusher device. In this case the sensor device placed on the pusher device is subjected to a force defined by the force by which the anti-siphon arm presses the piston against the pusher device and hence into abutment with the sensor device of the pusher device.

During the second diagnosis routine, an obtained sensor signal is compared to an expected sensor signal, the expected sensor signal corresponding to the expected, predefined load by which the anti-siphon arm presses the piston of the syringe towards the pusher device and hence towards the sensor device placed on the pusher device. If during the comparison it is found that the obtained sensor signal substantially deviates from the expected sensor signal, this deviation can be recorded and hence logged such that it may be read out from storage by a user or may be reported by the infusion device during regular reporting. In addition or alternatively, it is possible that the infusion device generates a message indicating that maintenance of the infusion device is advisable. This message may for example be displayed on a display of the infusion device, or it may be sent to a maintenance service, for example via a suitable communication network such as the Internet (the maintenance service may be outside of a healthcare institution in which the infusion device is used). In addition or alternatively, operation of the infusion devices could terminated, hence preventing a functioning of the infusion device, due to possibly unreliable force measurements during an infusion operation.

Dependent on the amount of deviation of the obtained sensor signal from the expected sensor signal, different measures may be initiated. If the deviation is small, only a recording of the mismatch may be performed. If the deviation is substantial, a message may be generated that maintenance is advisable. And if the deviation is so large that a reliable force measurement is not guaranteed, operation of the infusion device may be prohibited.

The anti-siphon arm may be constituted, in one embodiment, to press the piston towards the sensor device in order to bring the piston into abutment with the sensor device or with a pressure transmitting element constituted to act onto the sensor device. The anti-siphon arm herein, typically, exerts a predefined force onto the piston in order to bring it into abutment with the sensor device and hence to operatively connect it with the pusher device. In order to ensure that the force of the anti-siphon arm exerted onto the piston is substantially constant, the anti-siphon arm may be displaceably mounted on a sensor support of the sensor device. The anti-siphon arm may for example be pivotably arranged on the pusher device such that it can be moved between a non-activated, released position in which no operative connection between the piston and the pusher device is established, and an activated position in which an operative connection between the piston and the pusher device is established. The anti-siphon arm herein may be on the one hand pivotably mounted on the sensor support of the sensor device, and on the other hand may be elastically pretensioned with respect to the sensor support axially along its pivoting axis, such that the anti-siphon arm elastically presses the piston towards the pusher device and into abutment with the sensor device when the anti-siphon arm is in the activated position.

The sensor device may be constituted for example by a load cell. The sensor device, for this, may comprise a sensor support for example made from a metallic body, such as an aluminum body. On the surface of the sensor support, herein, at least one sensor element for example in the shape of a strain gauge or an extension gauge is placed. For example, in one embodiment, four sensor elements being placed on the sensor support are arranged to form a so-called Wheatstone bridge circuit having nodes in between which the sensor signal is obtained. The sensor elements may for example be bonded, e.g. glued, onto the sensor support. When the sensor device is subjected to a load, the sensor support is deformed, causing for example two sensor elements to be stretched and to further sensor elements to be contracted. The stretching/contracting of the sensor elements causes an electrical voltage signal in between the nodes of the bridge circuit, which is proportional to the force exerted onto the sensor device and hence may be processed to derive a force measurement.

The object is also achieved by a method for operating an infusion device for administering a medical fluid to a patient, wherein in the method:
- a pumping mechanism exerts a force onto a delivery set for delivering a medical fluid from the delivery set towards a patient,
- a sensor device measures the force exerted on the delivery set by the pumping mechanism, the sensor device being constituted to output a sensor signal indicative of the force exerted onto the delivery set, and
- a processor device controls operation of the infusion device.

Herein, during a diagnosis routine a sensor signal of the sensor device is obtained and compared to an expected sensor signal, to allow for detecting a drift in the sensor signal of the sensor device.

The advantages and advantageous embodiments described above for the infusion device equally apply also to the method such that it shall be referred to the above.

The idea of the invention shall subsequently be described in more detail with reference to the embodiments shown in the figures. Herein:

Figure 1:
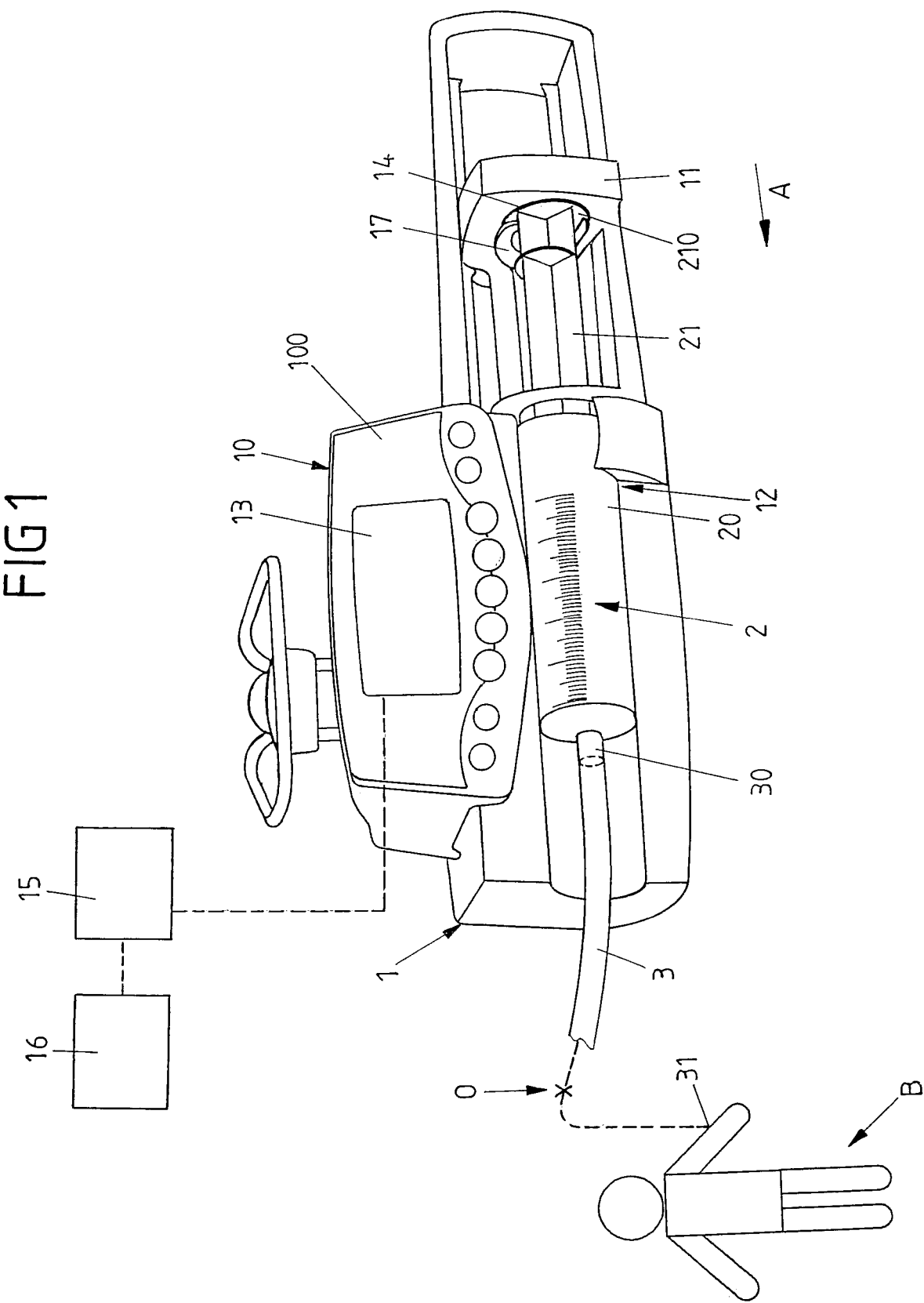
FIG. 1 shows a view of an infusion device constituted as a syringe pump.

FIG. 1 shows an embodiment of an infusion device 1 in the shape of a syringe pump. The infusion device 1 comprises a housing 10 having a front face 100 and a display device 13 arranged thereon. The display device 13 may for example be a touch-sensitive display allowing a user to enter commands for operation of the infusion device 1 and displaying operational information regarding the process of an actual infusion operation.

The infusion device 1 comprises a receptacle 12 in which a syringe 2 having a cylindrical tube 20 is arranged. A piston 21 is movable within the cylindrical tube 20 and is in engagement with a pusher device 11 of a pumping mechanism of the infusion device 1. At an end of the cylindrical tube 20 opposite the piston 21 a delivery line 3 extends from the cylindrical tube 20 towards a patient B, the delivery line 3 being connected to the cylindrical tube 20 at a first end 30 and to the patient B at a second end 31.

The piston 21 comprises a head 210 facing away from the cylindrical tube 20 and being in abutment with the pusher device 11 of the infusion device 1. During operation of the infusion device 1, the pusher device 11 is electromotorically driven in an actuation direction A such that the piston 21 is moved into the cylindrical tube 20 and a medical fluid contained in the cylindrical tube 20 is delivered via the delivery line 3 towards the patient B.

The infusion device 1 comprises a processor device 15 and a storage device 16. Via the processor device 15 the infusion operation of the infusion device 1 is controlled. In the storage device 16 operational parameters, such as mechanical characteristics of the syringe 2 used on the infusion device 1 as well as operational data, may be stored.

During an infusion process a medical fluid, for example a medication or a nutritional fluid for the parenteral feeding of a patient or the like, is delivered from the cylindrical tube 20 via the delivery line 3 towards the patient B. For this, the piston 21 is continuously pushed into the cylindrical tube 20 in the actuation direction A such that a desired flow rate is obtained, which is programmed by a user prior to the start of the infusion operation.

The delivery line 3 generally is made of a flexible tubing made for example from a PVC material. The delivery line 3 extends from the cylindrical tube 20 to the patient B and is, at its first end 30, in fluid connection with the cylindrical tube 20 and, at its second end 31, for example connected to a needle for providing an intravenous access to the patient B. During an infusion process an occlusion O in the delivery line 3 must be avoided and, if it nevertheless occurs, must be detected such that appropriate countermeasures to overcome the occlusion O can be taken. For this, a force sensor 14 is placed on the pusher device 11 facing the head 210 of the piston 214 measuring a force exerted on the piston 21 during an infusion process. From a force measured by means of the force sensor 14 an estimate of the pressure within the syringe 2 can be obtained, such that the pressure within the syringe 2 and the delivery line 3 can be monitored. If it is found that the pressure within the syringe 2 and the delivery line 3 rises beyond a permissible threshold value, an alarm is triggered indicating that an occlusion O may be present in the system.

Generally, the pressure in the delivery line 3 is very small (almost 0) during normal infusion operation in case no occlusion O is present. If an occlusion O occurs, the pressure will start to rise and will continue to rise (if the occlusion O does not disappear) until a threshold value is exceeded, at which moment an alarm is triggered by the processor device 15 such that a user is warned of the occlusion O.

To observe the pressure in the delivery line 3, the force applied to the piston head 210 of the piston 21 by means of the pusher device 11 is measured by the sensor 14. The force measured in this way allows for an indirect measurement of the pressure within the cylindrical tube 20, which generally equals the pressure in the delivery line 3.

In particular, the pressure in the cylindrical tube 20 depends on the measured force according to the following relation:

$$P = \frac{F - F_0}{S}.$$

Herein, P denotes the pressure, F denotes the measured force, $F_0$ denotes a frictional force component and S denotes the effective surface by which the piston 21 acts onto the liquid contained in the cylindrical tube 20. The effective surface S is substantially determined by the inner diameter of the cylindrical tube 20.

By determining the pressure in this way and by comparing the determined pressure P to a predefined threshold it can then be concluded whether an occlusion O is present in the delivery line 3 or not. In particular, if it is found that the pressure rises above the threshold, it is concluded that an occlusion O is present.

Whereas F is measured and S is known from the geometrical dimensions of the cylindrical tube 20 of the syringe 2, the frictional force component $F_0$ can for example be obtained from a calibration on a particular syringe or doing a statistical analysis of multiple syringes of the same or different kinds, brands and volumes.

Figure 2:
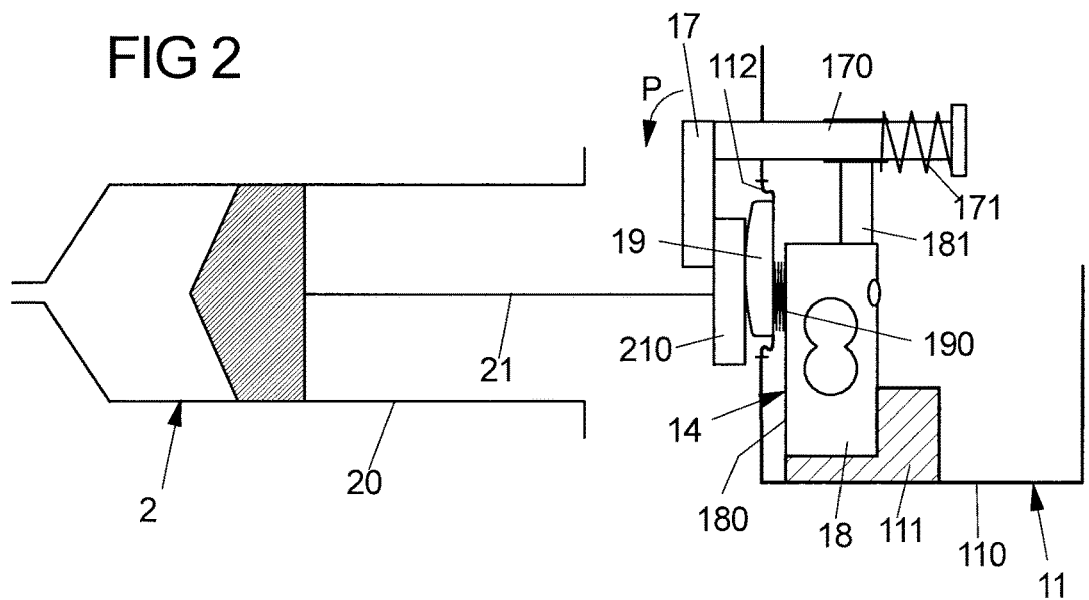
FIG. 2 shows a schematic drawing of a pumping mechanism of the infusion device.

FIG. 2 shows, in a schematic drawing, the mechanics of an embodiment of a pusher device 11 of the infusion device 1. The pusher device 11 comprises a housing 110 and is movable along the actuation direction A during an infusion operation to push the piston 21 at a constant speed into the cylindrical tube 20 of the syringe 2 in order to deliver a medical fluid from the cylindrical tube 20 at a constant dose rate towards the patient B. The pusher device 11 herein is driven by a suitable driving mechanism comprising an electric drive (not shown) controlled by the processor device 15.

For pushing the piston 21 into the cylindrical tube 20, the piston 21 via its piston head 210 is operatively connected to the pusher device 11 via an anti-siphon arm 17 mounted on the pusher device 11. The anti-siphon arm 17 is pivotably mounted via a shaft 170 on a sensor support 18 of the sensor device 14. The shaft 170, for this, is mounted on a support member 181 integrally connected with the sensor support 18 such that the shaft 170 is pivotable with respect to the support member 181, and in addition is axially displaceable along its pivoting axis (by at least a small margin).

The shaft 170 is pretensioned with respect to the support member 181 via a spring element 171 providing a spring elastic force axially on the shaft 170. The anti-siphon arm 17 herein is pivotable from a non-activated, released position in which the anti-siphon arm 17 does not act onto the piston head 210 for connecting it to the pusher device 11 into an activated position in which the anti-siphon arm 17 is pivoted in the pivoting direction P to act onto the piston head 210. In the activated position the anti-siphon arm 17 exerts a force axially onto the piston head 210 along the pivoting axis, caused by the spring element 171, in order to press the piston head 210 into abutment with a pressure transmitting element 19 which is elastically supported, via a spring element 190, on a front face 180 of the sensor support 18 of the sensor device 14 and acts onto the sensor device 14 to transmit a pressure towards the sensor device 14.

The pressure transmitting element 19 is sealed with respect to the housing 110 of the pusher device 11 by means of a sealing membrane 112 extending from the pressure transmitting element 19 and surrounding the pressure transmitting element 19. The inside of the housing 110 of the pusher device 11 hence is closed towards the outside to prevent entrance of moisture and dirt.

The piston 21 is, via the pressure transmitting element 19, in operative abutment on the sensor device 14 such that the sensor device 14 may measure a force exerted on the piston head 210 of the piston 21 by means of the pusher device 11. The sensor support 18 is mounted within the housing 110 a means of a mounting element 111 such that the sensor support 18 is fixedly connected to the housing 110 of the pusher device 11.

As described above, via the force sensor 14 the force acting onto the piston 21 is measured, thus allowing for estimating the pressure within the cylindrical tube 20 and within the delivery line 3, such that an occlusion in the delivery line 3 can be detected by observing the pressure.

Figure 3:
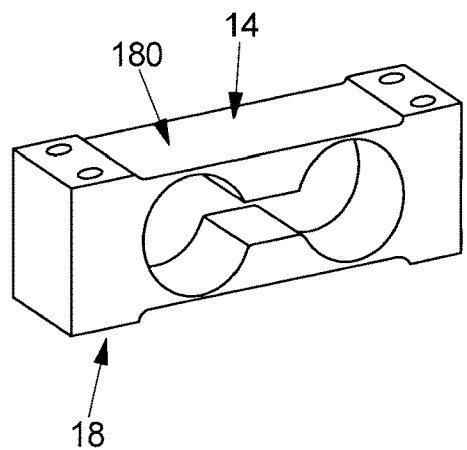
FIG. 3 shows a sensor device in the shape of a load cell.
Figure 4:
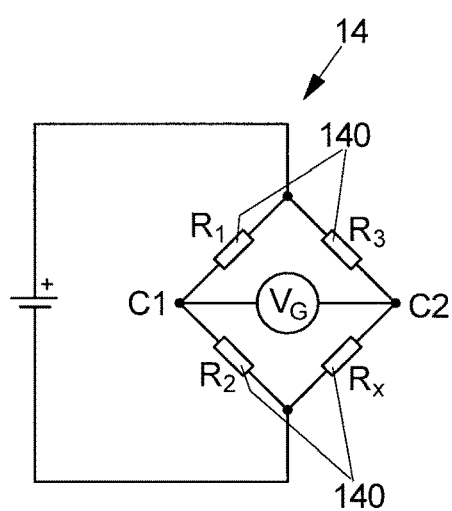
FIG. 4 shows an electric circuit schematic of the sensor arrangement.

The sensor device 14, in the illustrated embodiment, has the shape of a load cell, the sensor support 18 being formed by an integral metal body made for example from aluminum and having a front face 180 on which an arrangement of sensor elements 140 is placed, as depicted in FIGS. 3 and 4. The sensor elements 140 in the shape of strain gauges or extension gauges may be electrically connected, as shown in FIG. 4, to form a Wheatstone bridge having nodes C1, C2 in between which an electric voltage signal can be obtained, the voltage signal being proportional to the force exerted on the sensor device 14.

When a force is exerted on the sensor device 14, the sensor support 18 will be elastically deformed, which will lead to a stretching of some of the sensor elements 140 and to a contracting of the other sensor elements 140. Such stretching/contracting causes a voltage signal in between the nodes C1, C2, which can be picked up and can be used to derive a force measurement.

Within such load cells, a drift may occur, caused by a varying temperature or by aging effects over the lifetime of the sensor device 14. Such drift may have an effect on the accuracy of a force measurement, such that a drift should be detected and potentially be corrected.

Herein, two different kinds of drifts may occur, namely a zero drift and a span drift. The zero drift occurs when no force is exerted on the sensor device 14. The span drift, in contrast, occurs when a force is exerted on the sensor device 14.

To be able to detect a drift of the sensor signal, it is proposed to perform a diagnosis routine which enables the infusion device 1 to detect a drift and potentially correct a drift.

Herein, different diagnosis routines may be carried out, the different diagnosis routines allowing to detect a zero drift on the one hand and a span drift on the other hand.

In a first diagnosis routine, a sensor signal of the sensor device 14 is obtained when no syringe 2 is arranged on the infusion device 1 such that the pusher device 11 is not in operative connection with a piston 21 of a syringe 2. In this case the sensor device 14 is not loaded, such that the sensor signal of the sensor device 14 should be at or at least close to a stored zero reference, namely the reference sensor signal of the sensor device 14 while the sensor device 14 is not subjected to force. If it is found that the sensor signal obtained during the first diagnosis routine deviates from the stored zero reference by more than an allowable margin, the zero reference can be corrected making use of the obtained sensor signal, wherein in a first variant the stored zero reference may simply be replaced by the actually obtained sensor signal or in a second variant the stored zero reference may be updated making use for example of an infinite impulse response (IIR) filter.

During the first diagnosis routine, the obtained sensor signal is compared to the stored zero reference. Herein it can be checked whether the obtained sensor signal lies outside of a range around the stored zero reference. If this is the case, the zero reference is updated.

The first diagnosis routine is carried out controlled by the control device 15, which is programmed by software to perform the first diagnosis routine. The first diagnosis routine herein is carried out while no infusion operation is performed and, beneficially, while no syringe 2 is placed on the infusion device 1.

The infusion device 1 can automatically detect if a syringe 2 is placed on the infusion device 1 or not, for example by sensing the position of the anti-siphon arm 17. The first diagnosis routine may for example be carried out only if the anti-siphon arm 17 is in the non-activated, released position.

Alternatively or in addition, the control device 15 may be programmed to carry out a second diagnosis routine to detect a span drift of the sensor device 14. This second diagnosis routine is carried out when a syringe 2 is placed on the infusion device 1 and when the piston 21 of the syringe 2 is in operative connection with the pusher device 11 by fixing the piston 21 to the pusher device 11 via the anti-siphon arm 17.

For fixing the piston 21 to the pusher device 11, the anti-siphon arm 17 is pivoted in the pivoting direction P around its pivoting axis such that the anti-siphon arm 17 acts onto the piston head 21 and presses it axially towards the pusher device 11. In the fully activated position, herein, the anti-siphon arm 17 will press the piston head 210 with a defined force towards the pressure transmitting element 19 and hence towards the sensor device 14, the defined force being determined by the elastic tensioning force of the spring element 171 which elastically tensions the shaft 170 axially with respect to the sensor support 18.

Since the force of the anti-siphon arm 17 is defined and will be (approximately) constant, the sensor device 14 should, when the piston head 210 is fixed to the pusher device 11, pick up a constant force measurement (at least as long as no infusion operation is being performed and the force hence is due solely to the connection force caused by the anti-siphon arm 17). If it is found that this force measurement varies, it therefore can be concluded that a span drift in the sensor device 14 is present.

Hence, during the second diagnosis routine, with the piston head 210 fixed to the pusher device 11 via the anti-siphon arm 17, a sensor signal is obtained and compared to an expected sensor signal, the expected sensor signal corresponding to the predefined force by which the anti-siphon arm 17 presses the piston head 210 towards the sensor device 14. If it is found that the obtained sensor signal substantially deviates from the expected sensor signal, it can be concluded that a span drift is present.

Herein, dependent on the amount of the deviation, different measures can be taken.

If the deviation is small, the deviation can simply be recorded and logged in a log file.

If the deviation is substantial, but not excessive, a message may be generated advising a user that maintenance should be carried out. Such message can for example be electronically sent (via the Internet) to a maintenance service outside of the healthcare institution, for example of a manufacturer of the infusion device 1, such that the maintenance service may be ordered to perform a maintenance.

If the deviation is large, as the most severe countermeasure a further operation of the infusion device 1 may be prohibited, because a force measurement may no longer be reliable and hence an occlusion may not reliably be detected. In this case also a high priority alarm may be triggered.

The expected sensor signal for the second diagnosis routine may for example be known from calibration. In particular, by calibration the force by which the antis anti-siphon arm 17 presses the piston head 210 towards the sensor device 14 can be measured and a corresponding expected sensor signal can be stored.

It can be provided that the second diagnosis routine is carried out only when the anti-siphon arm 17 is fully activated and hence, in a defined fashion, presses the piston head 210 towards the sensor device 14.

To increase reliability of the second diagnosis routine, the measurements can be repeated multiple times, wherein a countermeasure is initiated only if consecutive diagnosis measurements yield a mismatch of the obtained sensor signal from the expected sensor signal.

The second diagnosis routine can also be used to detect a failure of the sensor device 14 due to other effects than a drift. If for example the sensor device 14 with its sensor elements 140 arranged to form a Wheatstone bridge comprises a shortcut or an open circuit, this would be detected during the second diagnosis routine.

The idea underlying the invention is not limited to the embodiments described above, but may be carried out in an entirely different fashion.

In particular, diagnosis routines as proposed above are not limited to infusion devices in the shape of syringe pumps, but may be carried out also on other infusion devices such as volumetric (peristaltic) infusion pumps.

Also, the pumping mechanism of a syringe pump may have a different shape than described above. Similar diagnosis routines may be applied also in this case.

LIST OF REFERENCE NUMERALS

1 Infusion device
10 Housing
100 Front face
11 Pusher device
110 Housing
111 Mounting element
112 Membrane
12 Receptacle
13 Display device
14 Force sensor
140 Sensor element
15 Processor device
16 Storage device
17 Anti-siphon arm
170 Shaft
171 Spring element
18 Sensor support
180 Front face
181 Support member
19 Pressure transmitting element
190 Spring element
2 Pumping device (syringe)
20 Cylindrical tube
21 Piston
3 Delivery line
30, 31 End
A Actuation direction
B Patient
C1, C2 Nodes
O Occlusion
P Pivoting direction

The invention claimed is:

1. An infusion device for administering a medical fluid to a patient, comprising:
 a pump configured to exert a force onto a delivery set for delivering a medical fluid from the delivery set towards a patient,
 a sensor configured to measure the force exerted on the delivery set by the pump, the sensor being configured to output a sensor signal indicative of the force exerted onto the delivery set, and
 a processor configured to control operation of the infusion device,
 wherein the processor is configured to perform a diagnosis routine during which a sensor signal of the sensor is obtained and compared to an expected sensor signal, to allow for detecting a drift in the sensor signal of the sensor, the sensor signal is obtained while the pump is not in operative connection with the delivery set, and the sensor comprises a zero reference corresponding to the expected sensor signal when the pump is not in operative connection with the delivery set, wherein, if the comparison during the diagnosis routine yields that a difference of the sensor signal obtained and the expected sensor signal is larger than a first predefined threshold, the zero reference of the sensor is corrected.

2. The infusion device according to claim 1, wherein the delivery set comprises a syringe having a tube containing a medical fluid and a piston movable with respect to the tube, the infusion device comprising a receptacle for receiving the syringe and a pusher device for acting onto the piston for pumping the medical fluid from the tube towards a patient.

3. The infusion device according to claim 2, wherein the sensor is arranged on the pusher device, wherein the pusher device comprises an anti-siphon arm configured to fix the piston with respect to the pusher device.

4. The infusion device according to claim 3, wherein the processor is configured to perform a second diagnosis routine while the anti-siphon arm fixes the piston with respect to the pusher device.

5. The infusion device according to claim 4, wherein, dependent on the comparison during the second diagnosis routine, a mismatch between the obtained sensor signal and the expected sensor signal is recorded, a message is generated indicating that maintenance of the infusion device is advisable, and/or operation of the infusion device is terminated.

6. The infusion device according to claim 3, wherein the anti-siphon arm is configured to press the piston towards the sensor to bring the piston into abutment with the sensor or with a pressure transmitting element configured to act onto the sensor.

7. The infusion device according to claim 3, wherein the anti-siphon arm is displaceably mounted on a sensor support of the sensor received in or on the pusher device.

8. The infusion device according to claim 1, wherein the sensor comprises at least one sensor element configured as a strain gauge or an extension gauge.

9. The infusion device according to claim 1, wherein the sensor comprises a multiplicity of sensor elements electrically connected to each other to form a bridge circuit having nodes in between which the sensor signal is obtained.

10. A method for operating an infusion device for administering a medical fluid to a patient, the method comprising:

exerting by a pump a force onto a delivery set for delivering a medical fluid from the delivery set towards a patient, measuring by a sensor the force exerted on the delivery set by the pump, the sensor being configured to output a sensor signal indicative of the force exerted onto the delivery set, and controlling by a processor operation of the infusion device, wherein during a diagnosis routine a sensor signal of the sensor is obtained and compared to an expected sensor signal, to allow for detecting a drift in the sensor signal of the sensor, the sensor signal being obtained while the pump is not in operative connection with the delivery set, and the sensor provides a zero reference corresponding to the expected sensor signal when the pump is not in operative connection with the delivery set, and, if the comparison during the diagnosis routine yields that a difference of the sensor signal obtained and the expected sensor signal is larger than a first predefined threshold, the zero reference of the sensor is corrected.

* * * * *